United States Patent [19]

DeBastiani et al.

[11] Patent Number: 4,621,627
[45] Date of Patent: Nov. 11, 1986

[54] EXTERNAL AXIAL FIXATION DEVICE

[75] Inventors: Giovanni DeBastiani, Verona; Giovanni Faccioli, Monzambano; Roberto Aldegheri, San Giovanni Lupatoto; Lodovico R. Brivio, Castenedolo, all of Italy

[73] Assignee: Orthofix S.r.l., Verona, Italy

[21] Appl. No.: 692,577

[22] Filed: Jan. 18, 1985

[30] Foreign Application Priority Data

Dec. 18, 1984 [IT] Italy .................. 84975 A/84

[51] Int. Cl.⁴ .............................................. A61F 5/04
[52] U.S. Cl. ............................ 128/92 ZZ; 128/92 Z
[58] Field of Search .................. 128/92 R, 92 A, 92 E

[56] References Cited

U.S. PATENT DOCUMENTS

| Re. 31,809 | 1/1985 | Danieletto et al. | 128/92 A |
| 1,869,726 | 8/1932 | Youngren | 128/92 A |
| 2,346,346 | 4/1944 | Anderson | 128/92 A |
| 2,391,537 | 12/1945 | Anderson | 128/92 A |
| 2,702,031 | 2/1955 | Wenger | 128/92 A |
| 4,185,624 | 1/1980 | Gentile | 128/92 A |
| 4,187,841 | 2/1980 | Knutson | 128/92 A |
| 4,299,212 | 11/1981 | Goudfrooy | 128/92 EB |
| 4,308,863 | 1/1982 | Fischer | 128/92 A |
| 4,475,546 | 10/1984 | Patton | 128/92 A |

Primary Examiner—Gene Mancene
Assistant Examiner—C. W. Shedd
Attorney, Agent, or Firm—Hopgood, Calimafde, Kalil, Blaustein & Judlowe

[57] ABSTRACT

The invention contemplates an orthopedic axial-fixation device wherein an extended range of body-length adjustment is achieved using three mutually telescoping members which are keyed against relative rotation, thereby preserving the selectively clamped orientation of pin mounts having ball-joint connection to the ends of the body. Separate selective clamping is available for securing a given extended relation of inner and intermediate body members and for securing a given extended relation of the intermediate and outer body members. Jacking mechanism for precision length adjustment of the body also uses three mutually telescoping threaded members so configurated that rotation of one of these threaded members is operative to provide jack expansion or retraction which serves the fullest possible range of body-length adjustability.

16 Claims, 7 Drawing Figures

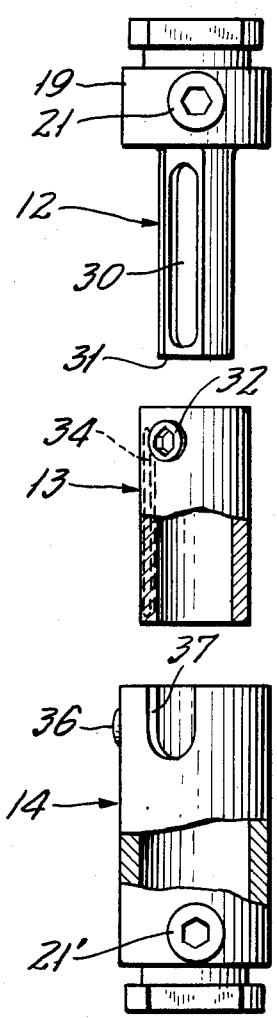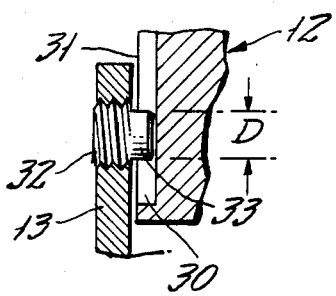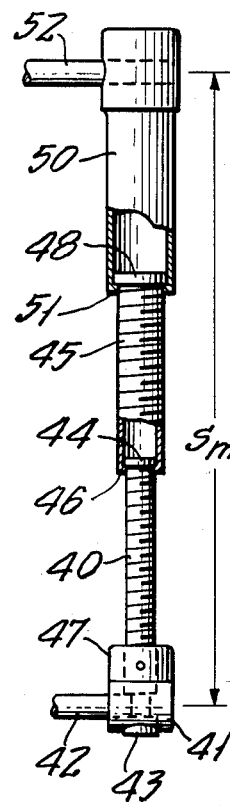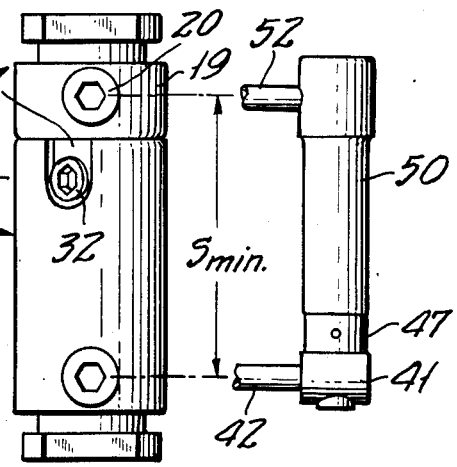

— 1 —

EXTERNAL AXIAL FIXATION DEVICE

BACKGROUND OF THE INVENTION

The present invention relates to orthopedic apparatus as for the external setting or securing of the parts of a fractured bone.

Danieletto, et al., U.S. Pat. No. 4,312,336 describes an orthopedic axial-fixation device in which a central body has inner and outer elongate cylindrical parts which have an angularly keyed telescoping relation, and pin mounts have ball-joint connection to the respective ends of the central body. Provision is made for selectively clamping the respective ball joints and for selectively clamping a given telescoped relation of the inner and outer parts. Provision is also made for selectively jacking (extending or retracting) the body length between ball joints. The patented device is well suited for application to fractures or similar problems affecting the larger bones, such as tibias and fibulas, particularly if the orthopedic surgeon or institution keeps an inventory of different body lengths, from which to select for use to meet a given orthopedic problem. But for smaller bones, such as the radius or ulna, wherein less bulk is desirable, and wherein it is also desirable to achieve a greater ratio of length adjustment with a single device (in order to avoid the requirement for an inventory of different body lengths, or of different-range body lengths), the design of the patented device is less than desirable.

BRIEF STATEMENT OF THE INVENTION

It is an object of the invention to provide an improved orthopedic axial-fixation device of the character indicated.

It is a specific object to achieve the above object with a construction inherently applicable to smaller-scale orthopedic problems and serving a range of available length adjustment and jack action which substantially exceeds the capabilities of prior devices.

It is a general object to achieve the above objects with a device that is basically simple to operate, for which a single tool will serve to make all necessary adjustments and to set all clamps, and which, when clamped, will accurately secure, space and orient the two bones or bone fragments involved in a given procedure.

The invention achieves the foregoing objects in an axial-fixation device of the general character of said Danieletto, et al. patent, but wherein the body portion of the device and the associated jacking mechanism each rely on multiple telescoping action. Specifically, inner, intermediate and outer cylindrical body parts are mutually telescoping and are keyed to retain the angular relation of ball-joint clamps at the respective body ends, whereby pinmount orientations at each end of the body remain true to a desired setting in spite of jacking action, over the full range of body-length adjustability. Also specifically, inner, intermediate and outer members of the jacking mechanism have mutually threaded engagement, so devised that by the simple expedient of driven rotation of the inner member, there results a full extensibility of all threaded engagements. The arrangement both for body extensibility and for jacking extensibility is such that the telescoping relationships and coaxial fidelity are preserved, throughout the full range of adjustability.

DETAILED DESCRIPTION

The invention will be described in detail for a preferred embodiment, in conjunction with the accompanying drawings, in which:

FIG. 3 is an exploded view of parts of the body of the device of FIGS. 1 and 2;

FIG. 3a is an enlarged fragmentary detail, in longitudinal section, to show a set screw and key relationship in the device of FIGS. 1 and 2;

FIG. 4 is a view in elevation of jacking mechanism, used with the device of FIGS. 1 and 2, and shown in fully extended relation;

FIG. 5 is a view of the body of FIG. 3, in fully compressed assembly; and

FIG. 6 is a view similar to FIG. 5, for the fully retracted condition of the jacking mechanism.

Figure 1:
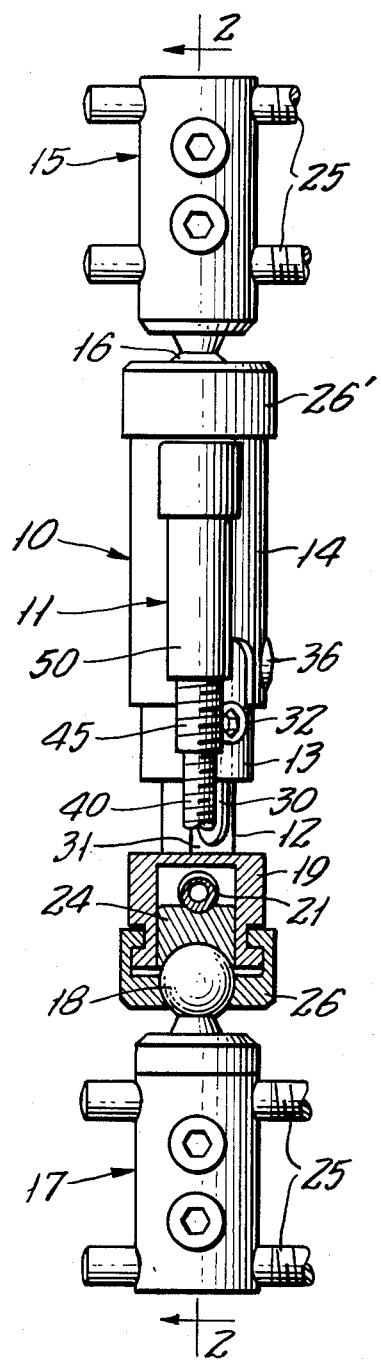
FIG. 1 is a view in longitudinal elevation of an axial fixation device of the invention, partly broken-away and in section to reveal an internal detail.
Figure 2:
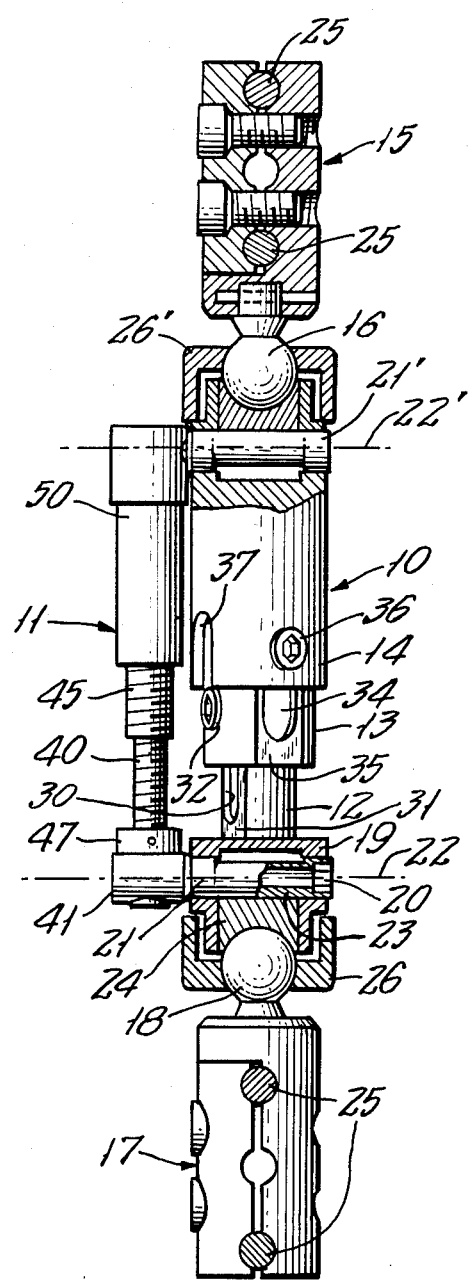
FIG. 2 is a view similar to FIG. 1, but taken at 90 degrees from the aspect of FIG. 1, with parts shown in section for the plane 2—2 of FIG. 1.

The orthopedic fixation device of FIGS. 1 and 2 is shown in a position of intermediate-length adjustment, wherein all three of the telescoping parts of its body 10 and all three of the telescoping parts of its length-adjusting jack mechanism 11 are partially exposed to view. The three telescoping body parts are an inner cylindrical member 12, an intermediate cylindrical sleeve 13, and an outer member 14 having a cylindrical bore which is capable of fully receiving the telescoped insertion of members 12 and 13. A first pin mount 15 has selectively engageable ball-joint connection at 16 to the closed end of outer body member 14, and a second pin mount 17 has similar selectively engageable ball-joint connection at 18 to the headed end 19 of the inner body member 12.

Quick releasable setting of a clamp for ball joint 16 relies on end access to a wrench-socket formation 20 at one end of the otherwise cylindrical bore of a tubular pin 21, which extends (on a pin axis 22) normal to the central axis of body 10 and which is journaled for rotation in the headed end 19 of inner body member 12. Between its spaced locations of journal support, pin 21 has an eccentric cylindrical formation 23 by which an engaged ball-joint seat member 24 may be jammed against the involved ball of the joint. The releasable clamp for the other ball-joint connection 18 is of similar construction, involving a tubular pin 21' journaled on a pin axis 22' in the closed upper end of outer body member 14.

Each of the pin mounts 15-17 is shown with two surgical pins 25, and when the eccentric lock of a pin 21 (21') is actuated to release its clamp, (1) the involved pin mount has universal freedom for orientation about its ball center, which is on the longitudinal body axis, or (2) the involved pin mount may be quickly disengaged from the body 10, by partial rotation of a ball-joint retaining ring 26 having bayonet engagement to the involved end of body 10. Further detail of surgical pins, pin mounts, and release mechanism therefor is contained in said U.S. Pat. No. 4,312,336.

The pin axes 22-22' are retained in parallel relation by reason of keyed anti-rotation engagement between the three body parts 12-13-14, as will become more clear upon reference to the exploded view of FIG. 3. In the case of inner body member 12, a relatively wide but shallow elongate flatbottomed groove 30 is formed in a chordal flat 31 in the outer cylindrical telescoping surface; groove 30 extends near but short of the full axial extent of the cylindrical surface.

In the case of intermediate sleeve 13, a radially adjustable set screw 32 near one axial end has an inner cylindrical end 33 of diameter D to pilot along the elongate lateral walls of groove 30; the inner end face of set screw 32 is flat, for relatively larger-area clamping engagement to the flat bottom of groove 30, to secure a clamped condition of sleeve 13 along inner member 12. Upon releasing set screw 32 from such clamped engagment to the groove bottom, the cylindrical end 33 remains as a guide key, thereby enabling adjustment of the telescope action within end limits of freedom for setscrew-end (33) accommodation in groove 30; should a further increase in telescopic expansion be desired, the flat end face of the set screw may be set against such involved area of the chordal flat 31 as exists at the adjacent end of the groove; in so doing, the keyed angular relation is maintained as between body parts 12–13, because the groove bottom and the chordal flat 31 are parallel. For a purpose which will become clear, the axis of radial action of set screw 32 and groove 30 engagement is at a first angular offset from parallelism to the parallel pin axes 22–22′.

The intermediate sleeve 13 is further characterized by a relatively wide but shallow elongate flatbottomed groove 34 (see FIG. 2) which is formed in a chordal flat 35 extending the full length of sleeve 13; groove 34 suitably is of the same width and depth dimensions as groove 30, and it extends near but short of the respective longitudinal ends of sleeve 13.

The open cylindrical telescoping end of outer body member 14 mounts a set screw 36 which may be a duplicate of set screw 32, for radial coaction with the groove 34 of intermediate sleeve member 13. Thus, as long as the cylindrical inner end of set screw 36 remains within the included volume of groove 34, a keyed relation is maintained between members 13–14, and telescoping action is retained between longitudinal limits of setscrew engagement with groove 34. Should a further increase in length in telescopic expansion be desired, the flat end face of the set screw 36 may be set against such involved area of the chordal flat 35 as exists at the adjacent end of the groove; and again, the keyed angular relation is maintained as between body parts 13–14. The axis of radial action of set screw 36 and groove 34 engagement is at a second angular offset from parallelism to the pin axes 22–22′, and a locally slotted end opening 37 in body member 14 at the above-mentioned first angular offset enables wrenching access to the inner set screw 32, even when the body members are in their fully telescoped relation (FIG. 5).

It is thus clear that all described parts of body 10, and associated ball joints and pin mounts, are retainable in unit-handling relation to facilitate involved length and angle relationships, and that once any of these relationships is decided upon, it may be secured by use of a single tool (e.g., an Allen wrench) applied to the set screw (32, 36) or clamp (21, 21′) of instantaneous concern. And if additional body length is desired beyond either or both of the groove-determined limits of telescopic expansion, the angularly keyed relation can still be retained even when one or both of the set screws (32–36) is clamped to the associated chordal flat (31–35).

For precision jacking, i.e., longitudinal expansion or reduction in length of body 10, it is preferred that the jacking mechanism 11 be removably applicable to the inner and outer body members 12–14. As with body 10, the jacking mechanism 11 comprises essentially three mutually telescoping parts, shown in FIGS. 1 and 2 in an intermediate position of adjustment, and in FIGS. 4 and 6 in their most extended and in their fully reduced relationships, respectively. As best seen in FIG. 4, an inner elongate member 40 is externally threaded for most of its longitudinal length; at one end, it is formed for axially retained rotational freedom with respect to a boss 41 which mounts a radial pin 42 that is sized for selective reception in the bore of one of the clamp pins 21–21′; the end 43 of inner member 40 will be understood to be exposed beneath boss 41 and to be formed with a wrench socket whereby preferably the same single wrench as used for all other settings may be received for rotary adjustment of member 40. At its other end, inner member 40 is formed with a short radially outward circular flange 44 which pilots on the cylindrical bore of an intermediate sleeve member 45. For further coaction with inner member 40, the lower end of sleeve member 45 is characterized by a short radially inward flange 46 having threaded engagement to inner member 40; the expanded limit of this engagement occurs on threaded drive to the point of flange 46 interference abutment with flange 44, while the contracted limit of this engagement occurs on threaded drive in the opposite direction to the point of flange 46 abutment with a collar 47 mounted to member 40 at adjacency to boss 41.

Intermediate sleeve member 45 is externally threaded for virtually its entire length, except that, at its other end, member 45 is characterized by a short radially outward circular flange 48 which pilots on the cylindrical bore of an outer sleeve member 50. For further coaction with sleeve member 45, the lower end of outer sleeve member 50 is characterized by a short radially inward flange 51 having threaded engagement to intermediate sleeve member 45; the expanded limit of this engagement occurs on threaded drive to the point of flange 51 interference abutment with flange 48, while the contracted limit of this engagement occurs on threaded drive in the opposite direction to the point of flange 51 abutment with collar 47, thus fully enclosing the intermediate sleeve member 45. It is preferred that in its fully enclosed condition, intermediate sleeve member 45 is accommodated to the point of abutment or near-abutment with a radial pin 52 at the upper end of outer sleeve member 50; pin 52 is, like pin 42, sized for selective reception in the bore of the other one of clamp pins 21–21′.

As indicated generally above, operation of the jacking mechanism 11 is via the single instrumentality of wrench rotation of inner member 40 via its wrenchsocketed end 43. Both thread engagements, namely at 40–46 and at 45–51, are preferably to the same pitch, so that whether a given turn (or turns) of the inner member 40 operates the engagement 40–46 or the engagement 45–51 is of no moment, because the same given proportional expansion or contraction of body length will occur. If one commences with the fully collapsed condition of FIG. 6, the engagement 45–51 may be the first to advance, and this advance may proceed to the point of flange-to-flange abutment at 48–51 before further wrench torque is operative to advance the engagement 40–46; at full advance, both flange abutments (48–51, and 44–46) will have occurred, accounting for a maximum span $S_{max}$ between the axes of pins 42–52. In an illustrative case, this maximum span $S_{max}$ is four inches, more than twice the minimum pin (42–52) span $S_{min}$ which applies for the fully shortened condition of body 10. For the same illustrative case, the unit-handling relation of telescoping body members is available for pin spans in this range and up to 3.75 inches, the remaining quarter inch being available via clamping to one or the other or both of the extreme chordalflat regions 31–35, as explained above. In all cases, it is to be noted that angularly keyed integrity of body 10 is assured.

In collapsing the jacking mechanism from its extreme expansion, wrench actuation of inner member 40 via its exposed socket at 43 may be operative first to drive the engagement 40–46, or first to drive the engagement 45–51; but it makes no difference which is first to occur. If engagement 40–46 is first to advance, it can continue until flange 46 abuts collar 47; beyond this point, further drive of inner member 40 is operative to advance the engagement at 45–51. If, on the other hand, the engagement 45–51 is first to advance, then it can continue until flange 48 abuts pin 52; beyond this point, further drive of inner member 40 is operative to advance the engagement at 40–46.

It will be seen that the described orthopedic axial fixator device meets all stated objects and provides an extended range of operational situations which can be served by one and the same unit-handling structure. Among other things, this means a greatly expanded range of available precision-length adjustments without requiring any change of given pin-mount orientations. And by providing the radial orientation of set screws (32–36) at angularly offset locations which are also angularly offset from the parallel clamp axes 22–22', one is assured that the radial pins 42–52 will so mount the jacking mechanism as to provide no interference with set-screw clamping; further, the jack-mounting pins 42–52 can serve the function of maintaining or adjusting body length, without interfering with wrench access to one or both of the ball-joint clamps 21–21'. The telescoping body parts are suitably of anodized machined aluminum, and the jack mechanism and clamp parts are all suitably of stainless steel.

While the invention has been described in detail for a preferred embodiment, it will be understood that modifications may be made without departing from the scope of the invention.

What is claimed is:

1. Orthopedic external fixation apparatus, comprising an elongate extendable central body comprised of inner, intermediate and outer telescopically related parts adapted to be concentrically guided and mutually displaceable along the longitudinal axis of said body and retained against relative rotation of said parts, a first pin mount connected via a ball joint to the outer part at one end of said body, a second pin mount connected via a ball joint to the inner part at the other end of said body, the centers of said ball joints being substantially on said axis, first selectively operable means for locking a given longitudinally telescoped relation of said inner and intermediate parts, second selectively operable means for locking a given longitudinally telescoped relation of said intermediate and outer parts, selectively operable means associated with each ball joint for locking a given orientation of the involved pin mount with respect to said body, and selectively operable jack mechanism operative between said inner and outer parts for controlled length adjustment of said body, said jack mechanism comprising inner, intermediate and outer elongate members concentrically related on a common elongation axis, a first threaded engagement between said inner and intermediate members and a second threaded engagement between said intermediate and outer members.

2. Orthopedic apparatus according to claim 1, in which (a) said outer member and said intermediate member each have an elongate cylindrical bore terminated by a radially inward internally threaded flange at one end, (b) said inner member and said intermediate member are each characterized by a threaded outer surface terminated by a radially outward flange at one end, the flanges of said intermediate member being at opposite ends and all threads being in the same direction of helical advance, the outer surface of said inner member being in threaded engagement with the inward flange of said intermediate member while the outward flange of said inner member is contained within the cylindrical bore of said intermediate member, and the outer surface of said intermediate member being in threaded engagement with the inward flange of said outer member while the outward flange of said intermediate member is contained within the cylindrical bore of said outer member.

3. Orthopedic apparatus according to claim 2, in which each of said outward flanges has coaxial piloting engagement with the cylindrical bore in which it is contained.

4. Orthopedic apparatus according to claim 2, in which first body-locating radial-pin means is carried at the outer-member end which is opposite the threaded-flange end thereof, said first radial-pin means being adapted for connecting said jack mechanism to the outer part of said central body, second body-locating radial pin means mounted to a connector which is axially fixed with respect to and freely rotatable about the inner-member end which is opposite the outward-flange end thereof, said second body-locating radial-pin means being adapted via said connector for connecting said jack mechanism to the inner part of said central body.

5. Orthopedic apparatus according to claim 4, in which the freely rotatable connection exposes the involved end of said inner member, and in which said exposed end is characterized by wrench formations adapted for wrenched drive of said inner member with respect to said radial pins.

6. In orthopedic external-fixation apparatus wherein an elongate extendable central body has inner and outer telescopically related parts adapted to be concentrically guided and relatively displaceable along the longitudinal axis of said body and retained against relative rotation of said parts, and wherein first and second pin mounts are ball-joint connected and releasably clamped to the respective ends of said body with ball-joint centers substantially on said axis, the improvement wherein an elongate sleeve concentric with said axis and radially interposed between and telescopically related to both said inner and outer parts is the means of concentric guidance of said inner and outer parts, a first selectively operable keying clamp coacting between said sleeve and said inner part for setting a selected longitudinal relation between said sleeve and said inner part, a second selectively operable keying clamp coacting between said sleeve and said outer part for setting a selected longitudinal relation between said sleeve and said outer part, the keying action of said clamps being the means of retention against relative rotation of said parts, and selectively operable jack mechanism operative between said inner and outer parts for controlled length adjustment of said body, said jack mechanism comprising inner, intermediate and outer elongate members concentrically related on a common elongation axis, a first threaded engagement between said inner and intermediate members and a second threaded engagement between said intermediate and outer members.

7. The improvement of claim 6, in which said first keying clamp comprises a set screw in a threaded radial opening in said sleeve, said inner part being characterized by an elongate groove in the outer surface thereof, said set screw being enterable into said groove, and in which said second keying clamp comprises a set screw in a threaded radial opening in said outer part, said sleeve being characterized by an elongate groove in the outer surface thereof, said last-mentioned set screw being enterable into said last-mentioned groove.

8. The improvement of claim 7, in which said outer part has a local access opening in register with said first set screw when said sleeve and outer part are in fully overlapping telescoped relation, whereby said first set screw is operable for said fully telescoped relation.

9. The improvement of claim 7, in which each of said grooves has a flat bottom and in which each associated set screw has a flat end engageable with the associated bottom in the clamped condition thereof.

10. The improvement of claim 9, in which each of said grooves is in a locally chordal flat formation of the involved part or sleeve, whereby, if necessary, one or both of said set screws may have clamped engagement to the associated chordal flat beyond the nearby limit of groove engagement.

11. The improvement of claim 7, in which each of said grooves terminates short of the associated end of the involved part or sleeve.

12. Orthopedic external-fixation apparatus, comprising an elongate extendable central body comprised of inner, intermediate and outer telescopically related parts adapted to be concentrically guided and mutually displaceable along the longitudinal axis of said body, means coacting between said telescopically related parts for retaining the same against relative rotation, a first pin mount connected via a ball joint to the outer part at one end of said body, a first ball-joint clamp at said one end of said body and including a rotatable clamp actuator on an axis normal to the longitudinal axis of said body, a second pin mount connected via a ball joint to the inner part at the other end of said body, a second ball-joint clamp at said other end of said body and including a rotatable clamp actuator on an axis normal to the longitudinal axis of said body and parallel to the rotatable clamp actuator for said first ball joint, and selectively operable jack mechanism including inner, intermediate and outer members having mutually telescoping threaded engagement, said jack mechanism being removably engageable at one end of its inner member to one end of said rotatable clamp actuators and being removably engageable at the opposite end of its outer member to the other of said rotatable clamp actuators.

13. Orthopedic apparatus according to claim 12, in which each of said rotatable clamp actuators has a cylindrical bore, and in which a radial pin at each end of said jack mechanism is the means of removable engagement to said body via the respective cylindrical bores of said clamp actuators.

14. Orthopedic apparatus according to claim 12, in which a first set screw on a first radially directed axis coacts between said inner and intermediate parts for securing a selected telescoped relation thereof, and in which a second set screw on a second radially directed axis coacts between said intermediate and outer parts for securing a selected telescoped relation thereof, said radially directed axes being at angular offset from each other and from parallelism to the axis of said rotatable clamp actuators.

15. Orthopedic external fixation apparatus, comprising an elongate extendable central body comprised of at least three telescopically related parts wherein said parts are adapted to be concentrically guided and mutually displaceable along the longitudinal axis of said body and retained against relative rotation of said parts, and wherein at least one of said parts is intermediate an inner part and an outer part, a first pin mount connected via a ball joint to the outer part at one end of said body, a second pin mount connected via a ball joint to the inner part of the other end of said body, the centers of said ball joints being substantially on said axis, first selectively operable means for locking a given longitudinally telescoped inner-to-intermediate part relation, second selectively operable means for locking a given longitudinally telescoped outer-to-intermediate part relation, selectively operable means associated with each ball joint for locking a given orientation of the involved pin mount with respect to said body, and selectively operable jack mechanism operative between said inner and outer parts for controlled length adjustment of said body, said jack mechanism comprising inner, intermediate and outer elongate members concentrically related on a common elongation axis, a first threaded engagement between said inner and intermediate members and a second threaded engagement between said intermediate and outer members.

16. Orthopedic external fixation apparatus, comprising an elongate extendable central body comprised of at least three telescopically related parts wherein said parts are adapted to be concentrically guided and mutually displaceable along the longitudinal axis of said body and retained against relative rotation of said parts, and wherein at least one of said parts is intermediate an inner part and an outer part, whereby coacting inner and outer concentric guide surfaces characterize the relation of each pair of radially adjacent telescoping parts, a first pin mount connected via a ball joint to the outer part at one end of said body, a second pin mount connected via a ball joint to the inner part at the other end of said body, the centers of said ball joints being substantially on said axis, separate selectively operable means for locking a given longitudinally telescoped relation of each pair of radially adjacent parts, selectively operable means associated with each ball joint for locking a given orientation of the involved pin mount with respect to said body, and selectively operable jack mechanism operative between said inner and outer parts for controlled length adjustment of said body, said jack mechanism comprising inner, intermediate and outer elongate members concentrically related on a common elongation axis, a first threaded engagement between said inner and intermediate members and a second threaded engagement between said intermediate and outer members.

* * * * *